(12) United States Patent
Blanz et al.

(10) Patent No.: US 7,847,544 B2
(45) Date of Patent: Dec. 7, 2010

(54) SYSTEM AND METHOD FOR MEASURING FORMATION TEMPERATURE AND/OR PRESSURE USING NUCLEAR QUADRUPOLE RESONANCE

(75) Inventors: Martin Blanz, Celle (DE); Carl Edwards, Katy, TX (US); Hyung Tae Kwak, Spring, TX (US)

(73) Assignee: Baker Hughes Incorporated, Houston, TX (US)

( * ) Notice: Subject to any disclaimer, the term of this patent is extended or adjusted under 35 U.S.C. 154(b) by 155 days.

(21) Appl. No.: 12/199,903

(22) Filed: Aug. 28, 2008

(65) Prior Publication Data

US 2009/0051359 A1 Feb. 26, 2009

Related U.S. Application Data

(63) Continuation-in-part of application No. 11/724,956, filed on Mar. 16, 2007, now Pat. No. 7,714,573.

(51) Int. Cl.
*G01V 3/00* (2006.01)
(52) U.S. Cl. .................................. 324/303; 324/300
(58) Field of Classification Search ................ 324/300, 324/303, 314, 315; 600/420; 166/264, 248, 166/53; 702/8
See application file for complete search history.

(56) References Cited

U.S. PATENT DOCUMENTS

| | | | |
|---|---|---|---|
| 3,528,000 A * | 9/1970 | Schwede | 324/303 |
| 4,710,713 A | 12/1987 | Strikman | |
| 4,710,714 A | 12/1987 | Weitekamp et al. | |
| 4,987,368 A | 1/1991 | Vinegar | |
| 5,233,300 A | 8/1993 | Buess et al. | |
| 5,365,171 A * | 11/1994 | Buess et al. | 324/307 |
| 5,629,623 A | 5/1997 | Sezginer et al. | |
| 5,712,566 A | 1/1998 | Taicher et al. | |

(Continued)

FOREIGN PATENT DOCUMENTS

WO 9906854 A3 2/1999

(Continued)

OTHER PUBLICATIONS

Hoult, D. I. (1979). "Rotating Frame Zeugmatography." Journal of Magnetic Resonance 33: 183-97.

(Continued)

*Primary Examiner*—Brij B Shrivastav
(74) *Attorney, Agent, or Firm*—Cantor Colburn LLP (57) ABSTRACT

A system for measuring at least one of a temperature and a pressure of an earth formation is disclosed. The system includes: a downhole tool disposed in a borehole and configured to be movable within the borehole; at least one nuclear quadrupole resonance (NQR) measurement device including a transmitter configured to emit a radiofrequency magnetic field having at least one selected frequency band into the earth formation to cause a component thereof to produce a NQR signal, and a detector configured to detect the NQR resonance signal; and a processor in operable communication with the measurement device and configured to generate NQR data from the NQR signal and calculate at least one of the temperature and the pressure of the earth formation therefrom. A method of measuring at least one of a temperature and a pressure of an earth formation is also enclosed.

21 Claims, 3 Drawing Sheets

U.S. PATENT DOCUMENTS

| | | | |
|---|---|---|---|
| 5,814,987 A | | 9/1998 | Smith et al. |
| 6,091,240 A | * | 7/2000 | Smith et al. .................. 324/300 |
| 6,104,190 A | | 8/2000 | Buess et al. |
| 6,166,541 A | | 12/2000 | Smith et al. |
| 6,247,542 B1 | | 6/2001 | Kruspe et al. |
| 6,522,135 B2 | | 2/2003 | Miller et al. |
| 6,686,737 B2 | | 2/2004 | Kruspe et al. |
| 6,952,096 B2 | | 10/2005 | Freedman |
| 7,265,550 B2 | | 9/2007 | Laubacher et al. |
| 7,425,827 B2 | | 9/2008 | Chen et al. |
| 7,714,573 B2 | * | 5/2010 | Edwards ..................... 324/303 |
| 2003/0071619 A1 | | 4/2003 | Sauer et al. |
| 2004/0124837 A1 | | 7/2004 | Prammer et al. |
| 2005/0162163 A1 | | 7/2005 | Mikhaltsevitch et al. |
| 2007/0244648 A1 | | 10/2007 | Chen |
| 2008/0073122 A1 | | 3/2008 | Blanz et al. |
| 2008/0110253 A1 | * | 5/2008 | Stephenson et al. ...... 73/152.19 |
| 2008/0224696 A1 | | 9/2008 | Edwards |
| 2008/0234937 A1 | | 9/2008 | Fang et al. |
| 2009/0200016 A1 | * | 8/2009 | Goodwin et al. ............ 166/248 |

FOREIGN PATENT DOCUMENTS

| | | |
|---|---|---|
| WO | 9919740 A1 | 4/1999 |
| WO | 9945409 A1 | 9/1999 |

OTHER PUBLICATIONS

Das, T. P. and E. L. Hahn (1958). Nuclear Quadrupole Resonance. New York, Academic Press, Inc. pp. 1-209.

Smith, J. A. S. (1971). "Nuclear Quadrupole Resonance Spectroscopy. General Principles." Journal of Chemical Education 48(1): 39-49.

Buslaeva, Y. A., E. A. Kravqenko, et al. (1987). "Nuclear quadrupole resonance in inorganic chemistry." Coordination Chemistry Reviews 82: 9-231.

Marino, R. A. and S. M. Klainer (1977). "Multiple spin echoes in pure quadrupole resonance." Journal of Chemical Physics 67(7): 3388-3389.

Lee, K. and W. Anderson (1967). Nuclear Spins, Moments, and Magnetic Resonance Frequencies. CRC Handbook of Chemistry and Physics. R. C. Weast and M. J. Astle. Boca Raton, Florida, CRC Press, Inc.: E66-68.

Huang, W. T. (1962). Petrology. New York, McGraw-Hill Book Company. Chapter 1. pp. 1-20.

Klainer, S. M., T. B. Hirschfeld, et al., "Fourier Transform Nuclear Quadrupole Resonance Spectroscopy", Fourier, Hadamard, and Hilbert Transforms in Chemistry, A. G. Marshall, New York Plenum Press: 147-182 (1982).

Petersen, G. L., "Pulsed nuclear quadrupole resonance instrumentation and study of the 14N spectrum and relaxation in sodium nitrite", Physics, Providence, Brown University: 1-221 (1975).

Cook, J. C. and J. R. Clements (1970). NQR borehole logging for evaporite minerals Third Symposium on Salt; vol. 2, Evaporated salt, solar salt, economic aspects, salt applications, rock physics-mechanics, subsidence, geophysics, hydraulic fracturing, mining J. L. D. Rau. Cleveland, OH N. Ohio Geol. Soc. : 353-356.

Marino, R. A., H. Wenk, et al. (1980). "Proposed applications of NQR techniques to the geosciences." Journal of Molecular Structure 58: 445-457.

Schempp, E., S. M. Klainer, et al. (1980). An Evaluation of Nuclear Quadrupole Resonance (NQR) Techniques for the In-Situ Measurement of Stress/Strain in Salt. Earth Sciences Division Annual Report, Lawrence Berkeley Laboratory. Report Analytic. No. LBL-12100.

Schempp, E., J. B. Murdoch, et al. (1981). Measurement of in-situ stress using NQR/NMR. Earth Sciences Division 1981 Annual Report, Lawrence Berkeley Laboratory. Report Analytic. No. LBL-13600.

Non Final Office Action for U.S. Appl. No. 11/724,956 (Mar. 16, 2007). Mailed Nov. 24, 2008.

International Search Report and Written Opinion, Mailed Apr. 8, 2010, International Appln. No. PCT/US2009/055274, Written Opinion 4 Pages, International Search Report 7 Pages.

\* cited by examiner

SYSTEM AND METHOD FOR MEASURING FORMATION TEMPERATURE AND/OR PRESSURE USING NUCLEAR QUADRUPOLE RESONANCE

CROSS REFERENCE TO RELATED APPLICATIONS

This application is filed under 37 CFR 1.53(b) as a continuation-in-part of and claims priority under 35 U.S.C. 120 to U.S. patent application Ser. No. 11/724,956 filed on Mar. 16, 2007, which is incorporated by reference herein in its entirety.

BACKGROUND

In hydrocarbon exploration operations, well boreholes are drilled by rotating a drill bit attached to a drillstring, and may be bored vertically or bored in selected directions via geosteering operations. Various downhole devices located in a bottomhole assembly (BHA) or other locations along the drillstring measure operating parameters, formation characteristics, and include sensors for determining the presence of hydrocarbons.

Temperature of the formation surrounding a borehole can have a significant impact on certain formation evaluation measurements, such as Nuclear Magnetic Resonance (NMR) measurements. The ability to accurately and timely measure the temperature of the formation would allow for modification of measurement parameters to increase the accuracy of certain formation evaluation measurements.

BRIEF DESCRIPTION OF THE INVENTION

A system for measuring at least one of a temperature and a pressure of an earth formation includes: a downhole tool disposed in a borehole and configured to be movable within the borehole; at least one nuclear quadrupole resonance (NQR) measurement device including a transmitter configured to emit a radiofrequency magnetic field having at least one selected frequency band into the earth formation to cause a component thereof to produce a NQR signal, and a detector configured to detect the NQR resonance signal; and a processor configured to generate NQR data from the NQR signal and calculate at least one of the temperature and the pressure of the earth formation therefrom.

A method of measuring at least one of a temperature and a pressure of an earth formation includes: disposing a downhole tool in a borehole; emitting a radiofrequency magnetic field having at least one selected frequency band into the earth formation to cause a component thereof to produce a NQR signal; detecting the NQR resonance signal; and calculating at least one of the temperature and the pressure of the earth formation from the NQR resonance signal.

BRIEF DESCRIPTION OF THE DRAWINGS

The following descriptions should not be considered limiting in any way. With reference to the accompanying drawings, like elements are numbered alike.

DETAILED DESCRIPTION OF THE INVENTION

The systems and methods described herein include Nuclear Quadrupole Resonance (NQR) sensors for downhole measurement of a temperature, pressure and/or composition of an earth formation. The NQR sensor measurements include, for example, NQR resonance frequencies and/or NQR relaxation times. The sensors, in one embodiment, are disposed with a downhole tool forming a part of a drillstring. The systems and methods, in some embodiments, include the capability to perform calculations, prepare temperature data and/or transmit the temperature data to a surface processor. The systems and methods may be utilized in real time to reliably measure the temperature and/or composition of the formation. The NQR or temperature data may be transmitted to the surface or stored in memory downhole for later evaluation when the bottom hole assembly is tripped out.

Figure 1:
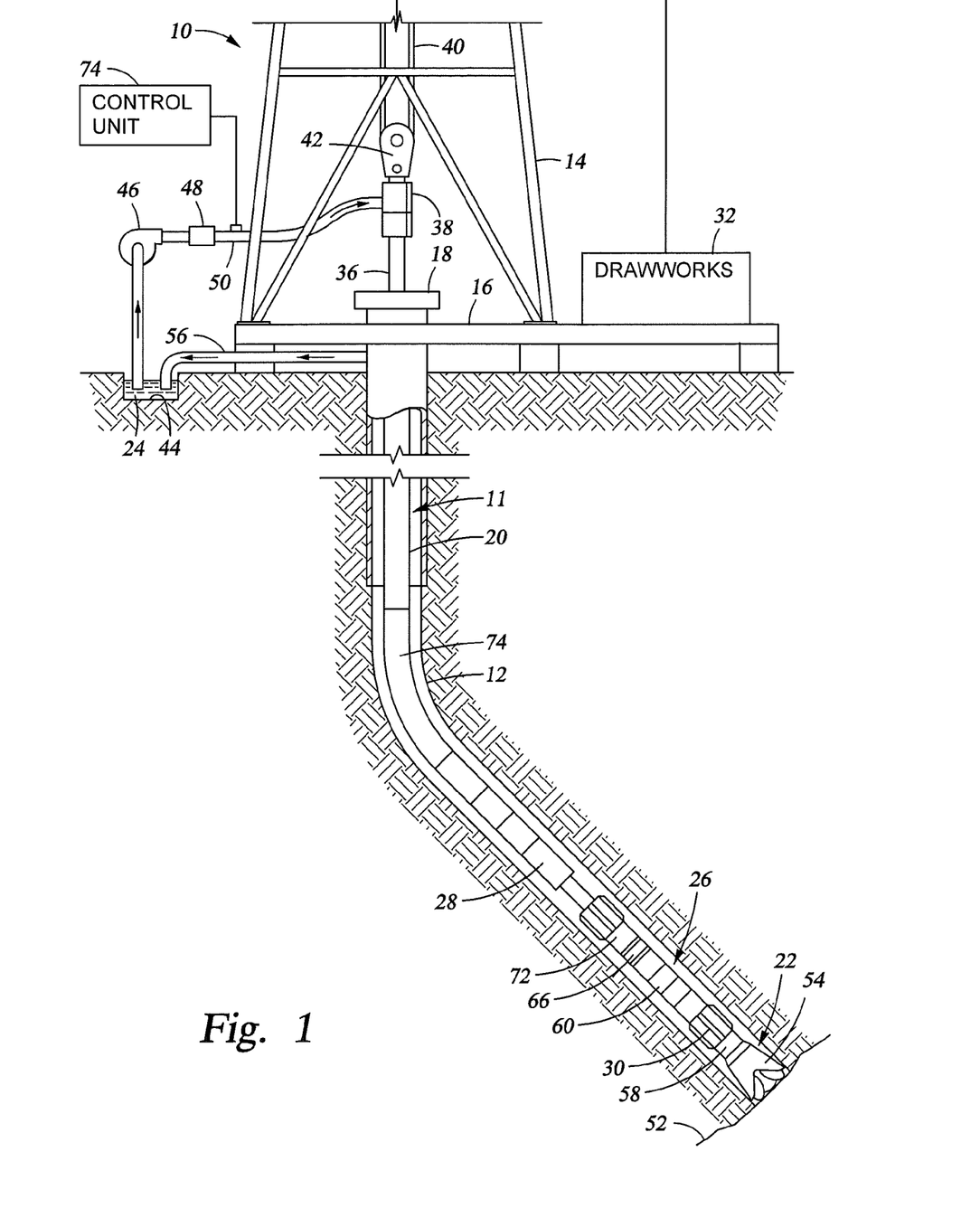
FIG. 1 is a side cross-sectional view of an embodiment of a drilling and/or geosteering system.

Referring to FIG. 1, an exemplary embodiment of a well drilling and/or geosteering system 10 includes a drillstring 11 that is shown disposed in a borehole 12 that penetrates at least one earth formation during a drilling operation and makes measurements of properties of the formation and/or the borehole 12 downhole. In one embodiment, such measurements are NQR measurements of temperature and/or other properties of the formation. Such NQR measurements include, for example, NQR resonance frequencies and NQR relaxation times.

As described herein, "borehole" or "wellbore" refers to a single hole that makes up all or part of a drilled well. As described herein, "formations" refer to the various features and materials that may be encountered in a subsurface environment and surround the borehole.

In one embodiment, the system 10 includes a conventional derrick 14 mounted on a derrick floor 16 that supports a rotary table 18 that is rotated by a prime mover at a desired rotational speed. The drillstring 11 includes one or more drill pipe sections 20 or coiled tubing that extend downward into the borehole 12 from the rotary table 18, and is connected to a drill bit assembly 22. Drilling fluid, or drilling mud 24 is pumped through the drillstring 11 and/or the borehole 12. The well drilling system 10 also includes a bottomhole assembly (BHA) 26.

The drill bit assembly 22 is powered by a surface rotary drive, a motor using pressurized fluid (e.g., a mud motor), an electrically driven motor and/or other suitable mechanism. In one embodiment, a drill motor or mud motor 28 is coupled to the drill bit assembly 22 via a drive shaft disposed in a bearing assembly 30 that rotates the drill bit assembly 22 when the drilling fluid 24 is passed through the mud motor 28 under pressure. The bearing assembly 30 supports the radial and axial forces of the drill bit, the downthrust of the drill motor and the reactive upward loading from the applied weight on bit.

In one embodiment, the drillstring 11 is coupled to a drawworks 32 via a kelly joint 36, a swivel 38 and a line 40 through a pulley 42. During the drilling operation the drawworks 32 is operated to control drilling parameters such as the weight on bit and the rate of penetration ("ROP") of the drillstring 11 into the borehole 12.

During drilling operations a suitable drilling fluid 24 from a mud pit 44 is circulated under pressure through the drillstring 11 by a mud pump 46. The drilling fluid 24 passes from the mud pump 46 into the drillstring 11 via, for example, a desurger 48, a fluid line 50 and the kelly joint 36. The drilling fluid is discharged at a borehole bottom 52 through an opening in a drill bit 54. The drilling fluid circulates uphole between the drill string 11 and the borehole 12 and is discharged into the mud pit 44 via a return line 56.

In one embodiment, the drill bit assembly 22 includes a steering assembly including a shaft 58 connected to the drill bit 54. The shaft 58, which in one embodiment is coupled to the mud motor, is utilized in geosteering operations to steer the drill bit 54 and the drillstring 11 through the formation.

In one embodiment, the drilling assembly 22 is included in the bottomhole assembly (BHA) 26, which is disposable within the well logging system 10 at or near the downhole portion of the drillstring 11. The BHA 26 includes any number of downhole tools 60 for various processes including formation drilling, geosteering, and formation evaluation (FE) for measuring versus depth and/or time one or more physical quantities in or around a borehole.

The downhole tool 60, in one embodiment, includes at least one nuclear quadrupole resonance (NQR) tool to measure a temperature of the formation. The downhole tool 60, in this embodiment, is configured to apply a radiofrequency magnetic field to a portion of the formation surrounding the downhole tool 60 and receive a NQR signal indicative of certain components. When the radiofrequency magnetic field covering at least one specific frequency band is applied to a certain substance, at least one resonance frequency is generated that is proportional to the electric quadrupole moment of a nucleus and to the electric field gradient present at the nucleus. The electric field gradient at the position of an NQR-active nucleus depends on the surrounding nuclei and electrons, hence on the chemical environment. Furthermore, the electric field gradient is dependent on the distance between atoms of a substance, which is temperature and pressure dependent. The NQR tool 60 is utilized as a thermometer to measure the temperature of the formation based on the detected resonance frequencies.

In another embodiment, the NQR tool 60 is configured to measure the temperature of the formation based on one or more detected NQR relaxation times. The NQR relaxation times include a least one of a longitudinal relaxation or spin lattice relaxation time "T1", a transversal or spin-spin relaxation time "T2", a free induction decay (FID) time "T2*", and a pulsed spin locking decay time "T2e". The formation temperature and/or pressure is calculated based on known relaxation times of known substances for specific temperatures and/or pressures. Examples of techniques for measuring NQR relaxation times are described in Klainer, S. M., T. B. Hirschfeld, et al., "Fourier Transform Nuclear Quadrupole Resonance Spectroscopy", *Fourier, Hadamard, and Hilbert Transforms in Chemistry*, A. G. Marshall, New York Plenum Press: 147-182 (1982), and Petersen, G. L., "Pulsed nuclear quadrupole resonance instrumentation and study of the $^{14}$N spectrum and relaxation in sodium nitrite", *Physics*, Providence, Brown University: 1-221 (1975), the disclosures of which are hereby incorporated by reference in its entirety.

In one embodiment, the downhole tool 60 also includes a nuclear magnetic resonance (NMR) tool. The formation temperature readings of the NQR tool can be used to calculate, for example, accurate NMR porosities from the NMR signals. In another embodiment, the downhole tool 60 also includes a Neutron Density (ND) tool. The formation temperature readings of the NQR tool can be used to calculate accurate Neutron Density porosities from the Neutron Density signals. The NMR tool is configured to apply both a static magnetic field and a radiofrequency magnetic field to generate NMR resonance signals from the formation. In one embodiment, the downhole tool 60 is capable of making both NMR and NQR measurements. In another embodiment, the NMR tool and the NQR tool are disposed at separate locations along the length of the drillstring 11 or other downhole assembly.

Although the NQR sensors are described in this embodiment as disposed within the drillstring 11, the NQR sensors may be used in conjunction with any structure suitable to lower the NQR sensors into a borehole, such as a wireline.

Figure 2:
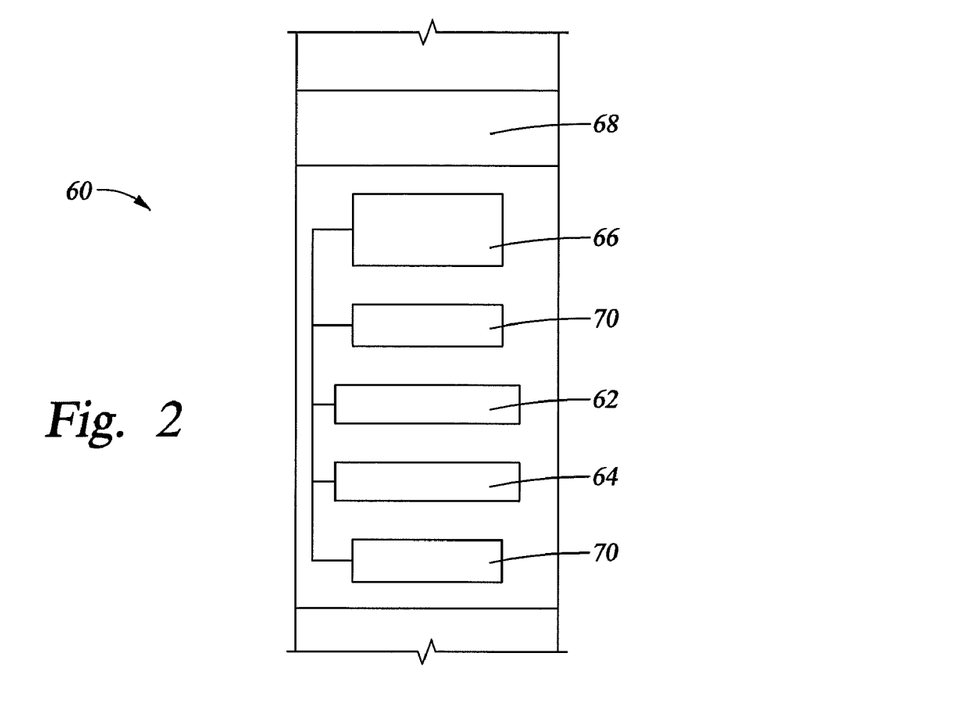
FIG. 2 is a side view of a downhole tool for measuring a temperature and/or composition of an earth formation.

Referring to FIG. 2, the NQR tool 60 includes one or more transmitting and/or receiving devices such as coils. The NQR tool 60, in one embodiment, includes coils that both transmit and receive or includes separate coils for transmitting and receiving. The transmitting coil provides a radiofrequency magnetic field that excites the quadrupole nuclei in the formation and results in their producing their characteristic resonance signals that are received by the receiving coil. In one embodiment, the coils are radio frequency (RF) coils for transmitting a pulsed RF field into the formation.

In one embodiment, the NQR tool 60 includes a transmitting coil 62 for applying the pulsed magnetic field to the formation and a receiving coil 64 to receive the resultant NQR resonance frequency signal. A processor or other electronics unit 66 is included to record, process and/or transmit the resultant NQR data. A power source 68 such as a wireline assembly, a battery assembly or mud-turbine-driven electrical generator is included to provide power to the NQR tool 60.

In one embodiment, the NQR tool 60 includes one or more permanent or switchable electrical magnets 70 for generating an external static magnetic field in addition to the RF magnetic field. In this embodiment, the NQR tool is configured to detect NQR-NMR double resonance signals. Any number of appropriate magnet arrangements and antenna or coil arrangements which provide static or switchable magnetic fields and/or a radiofrequency magnetic fields can be used.

Referring again to FIG. 1, in one embodiment, the tool 60 is equipped with transmission equipment 72 to communicate ultimately to a surface processing unit 74. In one embodiment, the surface processing unit 74 is configured as a surface drilling control unit which controls various drilling parameters such as rotary speed, weight-on-bit, drilling fluid flow parameters and others and records and displays real-time formation evaluation data. Such transmission equipment 72 may take any desired form, and different transmission media and connections may be used. Examples of connections include wired, fiber optic, wireless connections or mud pulse telemetry In one embodiment, the surface processing unit 74 and/or the tool 60 include components as necessary to provide for storing and/or processing data collected from various sensors therein. Exemplary components include, without limitation, at least one processor, storage, memory, input devices, output devices and the like. The surface processing unit 74 optionally is configured to control the tool 60.

Figure 3:
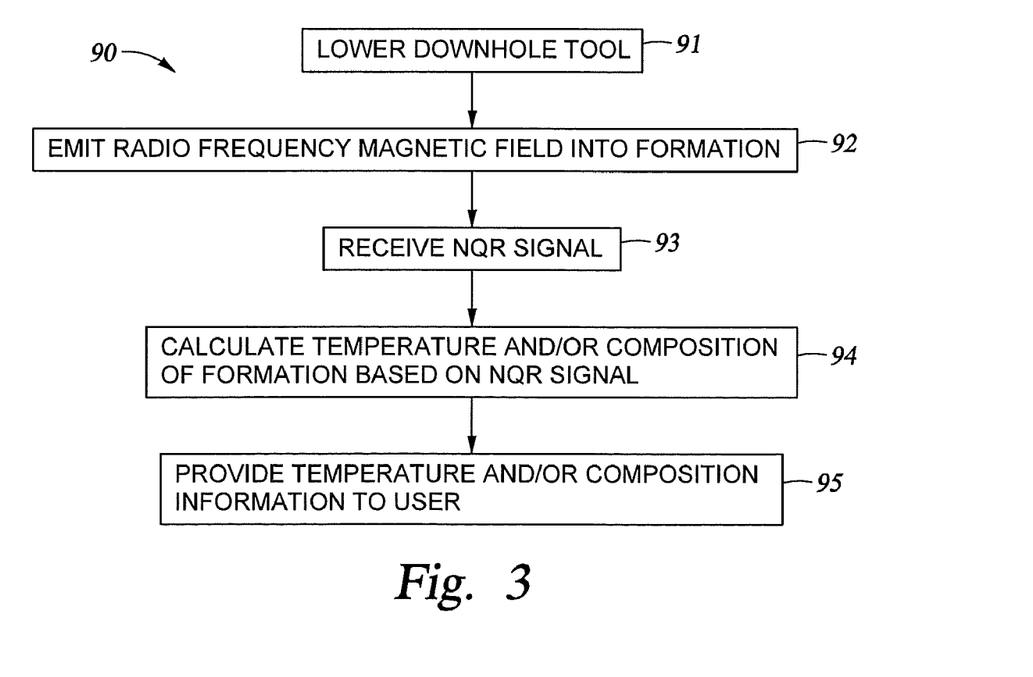
FIG. 3 is a flow chart providing an exemplary method of measuring a temperature and/or composition of an earth formation.

Generally, some of the teachings herein are reduced to an algorithm that is stored on machine-readable media. The algorithm is implemented by a computer or processor such as the surface processing unit 74 or electronics unit 66 and provides operators with desired output. For example, electronics unit 66 may store and process data downhole, or store data for later retrieval after the tool 60 is tripped out. In another example, data may be transmitted in real time to the surface processing unit 74 via wireline, or by any kind of telemetry such as mud pulse telemetry or wired pipes during an LWD operation FIG. 3 illustrates a method 90 for measuring a temperature and/or a composition of an earth formation. The method 90 includes one or more of stages 91-95 described herein. The method may be performed continuously or intermittently as desired. The method is described herein in conjunction with the NQR tool 60, although the method may be performed in conjunction with any number and configuration of processors, sensors and tools. The method may be performed by one or more processors or other devices capable of receiving and processing measurement data, such as the surface processing unit 74 or electronics unit 66. In one embodiment, the method includes the execution of all of stages 91-95 in the order described. However, certain stages 91-95 may be omitted, stages may be added, or the order of the stages changed.

In the first stage 91, the downhole tool 60 and/or the BHA 26 is lowered into a borehole during a drilling and/or geosteering operation.

In the second stage 92, the transmitter coil emits a radiofrequency magnetic field having at least one selected frequency bandwidth into the earth formation. In response, nuclei in certain molecules in the formation precess around an electric field gradient. The electric field gradient is generated by the nuclei and electrons in a molecule and is specific to the kind of molecule.

In the third stage 93, the receiver coil receives an NQR signal having a resonance frequency spectrum signal including one or more nuclear quadrupole resonance frequencies. In one embodiment, the resonance frequency spectrum includes one or more resonance frequencies corresponding to one or more types of substances. In another embodiment one or more of the relaxation times T1, T2, T2*, or T2e are measured.

In the fourth stage 94, the resonance frequency spectrum is compared to known resonance frequency values associated with known minerals or other substances to determine the presence of the substances. In one embodiment, the substances include crystalline substances found in the formation.

In one embodiment, the known resonance frequencies correspond to known substances at specific temperatures. A temperature of the formation is determined based on comparison with the known frequencies corresponding to known substances at specific temperatures. In another embodiment, one or more of the relaxation times T1, T2, T2* or T2e that were measured are used to determine the formation temperature. In yet another embodiment, the relaxation measurements are executed in addition to the measurement of the resonance frequencies.

In another embodiment, a pressure of the formation is measured to accurately determine the temperature corresponding to the resonance frequency spectrum. The pressure is measured by any suitable device such as a pressure sensor in the BHA 26 and a formation tester tool such as TesTrak™. The resonance frequency spectrum and/or relaxation times are then compared to the known frequencies and/or relaxation times corresponding to known substances at specific temperatures and pressures.

In another embodiment, both temperature and pressure are calculated from a plurality of NQR resonance frequencies and/or relaxation times. Temperature and pressure variation of different NQR substances may be different. In one example, resonance frequencies $f_1$ and $f_2$ are detected for two or more substances.

In another example, resonance frequencies $f_1$, and $f_2$ are measured from a single substance. In some substances, one or more types of NQR-active nuclei may be present, residing on more than one site in the molecule of the substance, the sites having different NQR resonance frequencies and different pressure and temperature dependence.

In this embodiment, temperature and pressure of the formation is calculated based on the linear approximation:

$$f_1 = \alpha_1 \Delta T + \beta_1 P + f_{01}$$

$$f_2 = \alpha_2 \Delta T + \beta_2 P + f_{02},$$

where "$f_1$" and "$f_2$" are first and second frequencies associated with either a first and second substance or a single substance having multiple resonance frequencies, "$\Delta T$" is a temperature difference in respect to a certain temperature where the NQR frequencies are $f_{01}$ and $f_{02}$ at zero pressure, "P" is pressure, "$\alpha_1$" and "$\beta_1$" are coefficients associated with the first frequency, and "$\alpha_2$" and "$\beta_2$" are coefficients associated with the second frequency. The parameters $\alpha_1$, $\beta_1$, $f_{01}$, $\alpha_2$, $\beta_2$ and $f_{02}$ are known or measured experimentally, they may be applicable for at least a certain temperature and pressure range and may be different for a different temperature or pressure range. In one embodiment, if more than two resonances are present, the equations are solved for $\Delta T$ and P using any suitable statistical analysis, including a non-linear or linear regression analysis method such as least squares. This analysis is applicable to both linear and non-linear dependence on pressure and temperature, and is applicable to both NQR resonance data and NQR relaxation time data.

In one embodiment, the resonance frequency spectrum and/or the relaxation measurements are compared to resonance frequencies and/or relaxation times associated with crystalline minerals known to occur in the formation in a relatively pure form, having a small concentration of defects in their crystal lattices, to reduce excessive broadening of the generated resonance spectrum lines and to avoid significant reduction of the relaxation rates.

In one embodiment, both resonance frequency and relaxation time measurements are utilized to calculate formation temperature. In another embodiment, the width of the NQR resonance frequency spectrum is utilized in conjunction with measured NQR relaxation times to produce information regarding a purity of the NQR-active substances in the formation.

In the fifth stage 95, the temperature and/or pressure is provided to a user and may be used to record and/or monitor the measured temperature, pressure and/or composition values of the formation. In one embodiment, the data is stored in the tool 60 and/or transmitted to a processor such as the surface processing unit 74, and can be retrieved therefrom and/or displayed for analysis. As used herein, a "user" may include a drillstring or logging operator, a processing unit and/or any other entity selected to retrieve the data and/or control the drillstring 11 or other system for lowering tools into a borehole.

In one embodiment, the taking of measurements from the tool 60 is recorded in relation to the depth and/or position of the downhole tool 60, which is referred to as "logging", and a record of such measurements is referred to as a "log". Examples of logging processes that can be performed by the system 10 and in conjunction with the methods described herein include measurement-while-drilling (MWD) and logging-while-drilling (LWD) processes, during which measurements of properties of the formations and/or the borehole are taken downhole during or shortly after drilling. Additional examples of logging processes include logging measurements after drilling, wireline logging, pipe-conveyed logging operations and drop shot logging. The data retrieved during these processes may be transmitted to the surface, and may also be stored with the downhole tool for later retrieval.

In one embodiment, the method 90 is utilized in conjunction with NMR measurements of the formation. In this embodiment, the tool 60 emits a measurement signal, i.e., a radiofrequency magnetic field, into the formation and receives a NQR signal indicative of certain constituent substances. From the specific position of the NQR resonance frequencies in the frequency spectrum the actual temperature in the formation may be deduced. In addition, the tool 60 or an additional tool emits a static magnetic field and a radiofrequency magnetic field, into the formation and receives a NMR signal indicative of, for example, the NMR formation porosity. As the NMR signal amplitude is proportional to the NMR porosity and inversely proportional to the formation temperature, the accurate NMR porosity can be calculated using the formation temperature that is measured by NQR. In one embodiment, the NQR measurement is performed as a NQR-NMR double resonance measurement, which may include field-cycling NQR-NMR double resonance measurements.

Figure 4:
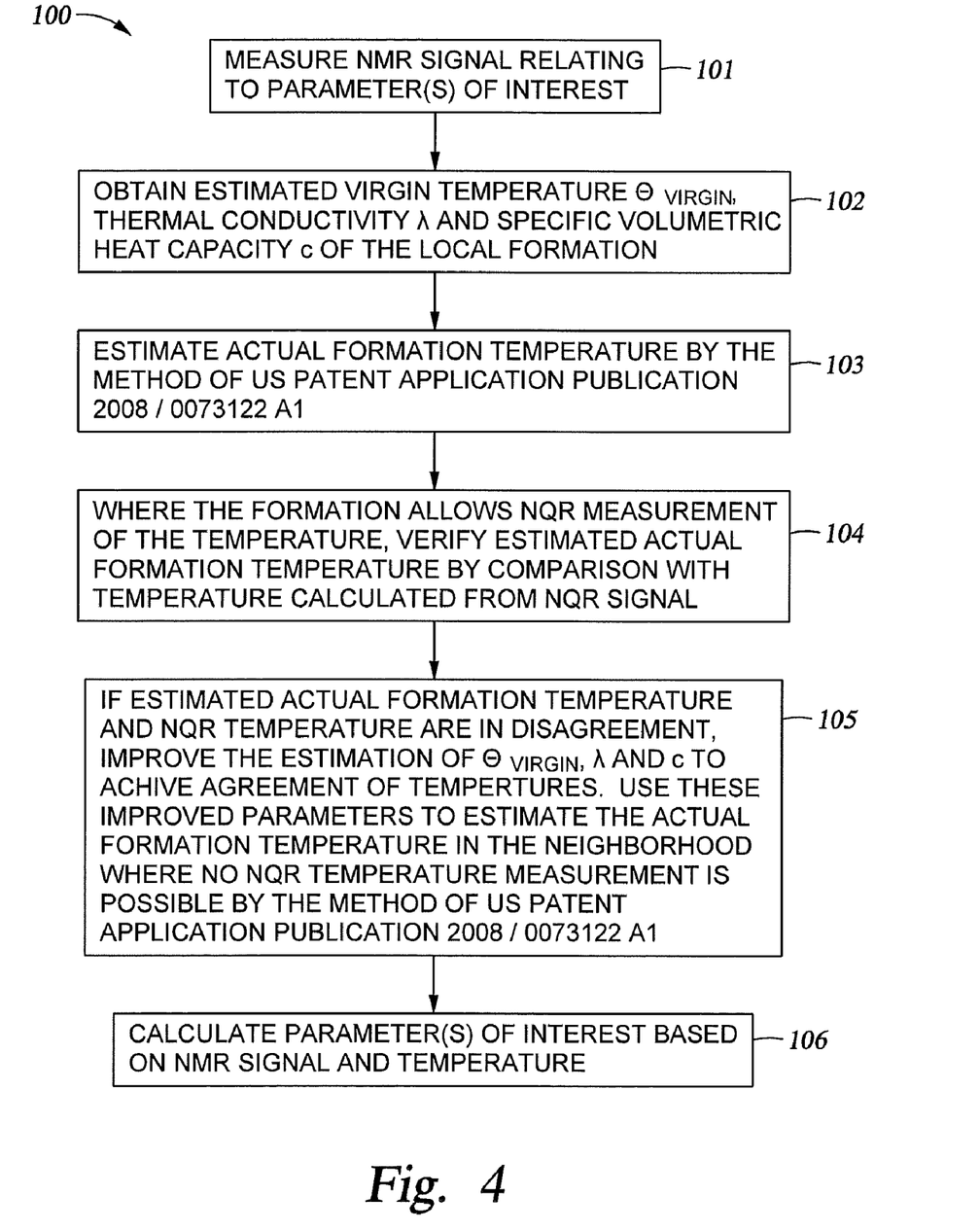
FIG. 4 is a flow chart providing another exemplary method of measuring a temperature and/or composition of an earth formation.

Referring to FIG. 4, in one embodiment, a method 100 is provided that utilizes NQR temperature measurements to estimate an actual formation temperature "$\Theta_{formation}$" at a time of a measurement of a parameter of interest. An example of estimating the actual formation temperature is described in US Patent Application Publication No. 2008/0073122 A1, published on Mar. 27, 2008, the disclosure of which is hereby incorporated by reference in its entirety. The method includes one or more stages 101-106. The actual formation temperature is based on a "virgin" temperature of the formation, a temperature of the drilling fluid and heat conduction in the formation. Such estimation may be utilized to compensate for changes in temperature of the formation due to heat conduction in portions of the formation surrounding the borehole.

In a first stage 101, one or more parameters of interest are measured in the borehole 12 and/or the earth formation. The measured parameters are any of various formation or borehole properties, such as formation evaluation properties including an NMR (i) porosity value, (ii) clay bound water value, (iii) bound water irreducible value, (iv) bound water moveable value, (v) diffusivity value, and/or (vi) permeability value, and/or an ND neutron density value, for example, from the measured FE signals.

In the second stage 102, the estimated virgin temperature and estimated parameters related to the thermal conduction in the formation is obtained. Such parameters include a thermal conductivity "$\lambda$" and a specific volumetric heat capacity "c" of the local formation. The formation temperature $\Theta_{formation}$ in a sensitive region of the downhole tool 60 (the "selected region") may not generally be the "virgin" formation temperature "$\Theta_{formation}^{virgin}$" because the temperature of the earth formation around the borehole 12 is often affected by the drilling mud 24. Also, the formation temperature $\Theta_{formation}$ is generally not constant over time. Before the earth formation has been drilled into, the formation temperature is the virgin formation temperature, i.e., $\Theta_{formation}=\Theta_{formation}^{virgin}$. However, after the borehole 12 has penetrated the earth formation, the drilling mud 24 generally cools the earth formation near the borehole 12. The mud temperature "$\Theta_{mud}(t)$" may be time-dependent and may be measured downhole by one or more downhole tools 60.

In one embodiment, the virgin temperature is obtained via an NQR measurement taken during or immediately after drilling through a specified depth or at a time that the NMR parameter is measured. In one embodiment, determining the virgin formation temperature of the earth formation further includes logging at least one nearby well by, for example, wireline. In another embodiment, the NQR measurement is taken at an elapsed time before or after the NMR parameter is measured. This may occur, for example, in BHAs having an NMR tool disposed a significant distance from an NQR tool in a drillstring.

In one embodiment, determining the actual formation temperature "$\Theta_{formation}$" of the earth formation includes measuring downhole mud temperature over time and/or depth. Examples of determining the virgin and actual formation temperatures are described in U.S. Patent Application Publication No. 2008/0073122 A1.

In the third stage 103, the actual formation temperature and/or a formation temperature transient is estimated. In one embodiment, the actual formation temperature "$\Theta_{formation}^{estimated}$" of the selected region is calculated based on one or more of a set of parameters, including (I) the virgin formation temperature $\Theta_{formation}^{virgin}$ of the earth formation, (II) the downhole mud temperature $\Theta_{mud}(t)$ over time, (III) the time elapsed $t_{elapsed}$ between drilling the borehole 12 and making the parameter measurement in the selected region, (IV) a thermal conductivity "$\lambda_{earth}$" of the earth formation, and (V) at least one of (i) a volumetric heat capacity "$c_{earth}^V$" of the earth formation and (ii) a specific heat capacity "$c_{earth}$" of the earth formation together with a density "$\rho_{earth}$" of the earth formation. Estimating the formation temperature $\Theta_{formation}^{estimated}$ of the earth formation includes using one or more of the set of the above-mentioned parameters (I)-(V) in at least one partial differential equation, at least one of whose solutions gives the estimated formation temperature $\Theta_{formation}^{estimated}$ (r,t) of the selected region, dependent on a radial distance "r" into the earth formation from the center of the borehole 12 and a time "t". Further description of this exemplary method for estimating temperature is provided in U.S. Patent Application Publication No. 2008/0073122 A1

In the fourth stage 104, in the instance where the actual formation temperature is estimated based on measurements of mud temperature described herein, an NQR measurement is used to verify the estimated actual formation temperature. For example, the temperature calculated from a NQR signal is compared to the estimated actual formation temperature to verify the accuracy of the estimation.

In the fifth stage 105, some estimated parameters that are the base of the actual formation temperature estimation are modified so that the estimated temperature calculated according to the method described in U.S. Patent Application Publication No. 2008/0073122 A1 agrees with the temperature measured by NQR. These improved parameters are subsequently used to estimate the actual formation temperature in the neighborhood where no NQR temperature measurement may be possible, e.g., due to lack of suitable NQR active substances in the formation.

In the sixth stage 106, the actual formation temperature at the time of measurement is used to calculate the parameter of interest. For example, an NMR signal is proportional to the NMR porosity and inversely proportional to the absolute temperature of the substance, such as the formation, in which NMR is measured. Accordingly, the actual formation temperature is used to calculate the NMR porosity. In another example, neutron density, which is also dependent on the formation temperature, is calculated using the actual formation temperature.

In one embodiment, the actual formation temperature is estimated by an exemplary method such as that described in U.S. Patent Application Publication No. 2008/0073122 A1. This alternative method for estimating temperature is used, for example, in instances where no NQR signal can be received due to lack of a suitable NQR-active formation. In another embodiment, the alternative method is utilized to estimate temperature of the formation, and an NQR signal is generated to calculate the temperature and verify the accuracy of alternative methods.

In one embodiment, the methods are performed during the drilling operation and yield real time information regarding downhole conditions. As used herein, generation of data in "real-time" is taken to mean generation of data at a rate that is useful or adequate for making decisions during or concurrent with processes such as drilling as may be opted for by a user or operator. As a non-limiting example, real-time measurements and calculations may provide users with information necessary to make desired adjustments during drilling and/or logging process. In one embodiment, adjustments are enabled on a continuous basis (at the rate of drilling), while in another embodiment, adjustments may require periodic cessation of drilling for assessment of data. Accordingly, it should be recognized that "real-time" is to be taken in context, and does not necessarily indicate the instantaneous determination of data, or make any other suggestions about the temporal frequency of data collection and determination.

The systems and methods described herein provide various advantages over prior art techniques. Use of NQR measurements allow for efficient and accurate measurement of formation properties and temperature. In addition, use of NMR and NQR in conjunction may allow for improved accuracy in measurement of constituent substances and temperature. For example, the signal amplitude of NMR measurements can be significantly affected by the formation temperature. Measurements such as total porosity determined by NMR are inaccurate if the formation temperature is measured (or assumed) inaccurate.

In support of the teachings herein, various analyses and/or analytical components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing aspects of the teachings herein. For example, a sample line, sample storage, sample chamber, sample exhaust, pump, piston, power supply (e.g., at least one of a generator, a remote supply and a battery), vacuum supply, pressure supply, refrigeration (i.e., cooling) unit or supply, heating component, motive force (such as a translational force, propulsional force or a rotational force), magnet, electromagnet, sensor, electrode, transmitter, receiver, transceiver, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A system for measuring at least one of a temperature and a pressure of an earth formation, the system comprising:
   a downhole tool disposed in a borehole;
   at least one nuclear quadrupole resonance (NQR) measurement device including a transmitter configured to emit a radiofrequency magnetic field having at least one selected frequency band into the earth formation to cause at least one component thereof to produce a NQR signal, and a detector configured to detect the NQR resonance signal; and
   at least one processor in operable communication with the measurement device and configured to generate NQR data from the NQR signal and calculate at least one of the temperature and the pressure of the earth formation based on a comparison of the NQR data and data associated with the at least one component.

2. The system of claim 1, wherein the NQR signal includes at least one of: i) one or more resonance frequencies corresponding to one or more specific substances at specific temperatures and ii) one or more relaxation times corresponding to one or more specific substances at specific temperatures.

3. The system of claim 2, wherein the at least one processor is configured to calculate at least one of the temperature and the pressure by at least one of: i) comparing the one or more resonance frequencies to resonance frequency values of known substances at known temperatures and ii) comparing the one or more relaxation times to relaxation time values of known substances at known temperatures.

4. The system of claim 1, wherein the measurement device includes at least one electrically conductive coil configured to at least one of: generate the radiofrequency magnetic field and detect the NQR signal.

5. The system of claim 1, wherein the measurement device includes at least one transmitter configured to generate the radiofrequency magnetic field and at least one detector to detect the NQR signal.

6. The system of claim 1, wherein the measurement device is configured to generate a Nuclear Magnetic Resonance (NMR) signal from the earth formation.

7. The system of claim 6, wherein the detector is configured to detect an NQR-NMR double resonance signal, and the at least one processor is configured to calculate the temperature of the earth formation from the NQR-NMR double resonance signal.

8. The system of claim 1, wherein the measurement device further includes a magnet assembly configured to provide a static magnetic field in the earth formation to produce a nuclear magnetic resonance (NMR), the detector is configured to detect the NMR signal, and the at least one processor is configured to generate NMR data and calculate a porosity of the earth formation based on the NMR data and the temperature.

9. The system of claim 1, wherein the at least one processor is disposed in a location selected from a downhole location and a surface location.

10. The system of claim 1, further comprising transmission equipment configured to transmit at least one of the calculated temperature and pressure to a user.

11. A method for measuring at least one of a temperature and a pressure of an earth formation, the method comprising:
   disposing a downhole tool in a borehole;
   emitting a radiofrequency magnetic field having a selected frequency into the earth formation to cause at least one component thereof to produce a nuclear quadrupole resonance (NQR) signal;
   detecting the NQR signal; and
   calculating at least one of the temperature and the pressure of the earth formation based on a comparison of the NQR signal and data associated with the at least one component.

12. The method of claim 11, wherein the NQR signal includes at least one of: i) one or more resonance frequencies corresponding to one or more specific substances at specific temperatures and ii) one or more relaxation times corresponding to one or more specific substances at specific temperatures.

13. The method of claim 12, wherein calculating at least one of the temperature and the pressure includes at least one of: i) comparing the one or more resonance frequencies to resonance frequency values of known substances at known temperatures and ii) comparing the one or more relaxation times to relaxation time values of known substances at known temperatures.

14. The method of claim 11, wherein at least one of emitting the radiofrequency magnetic field and detecting the NQR signal is performed by at least one electrically conductive coil.

15. The method of claim 11, wherein emitting the radiofrequency magnetic field is performed by at least one transmitter disposed in the downhole tool, and detecting the NQR signal is performed by at least one detector disposed in the downhole tool.

16. The method of claim 11, further comprising generating a Nuclear Magnetic Resonance (NMR) signal from the earth formation.

17. The method of claim 16, further comprising generating NMR data from the NMR signal and calculating a porosity of the earth formation based on the NMR data and the temperature.

18. The method of claim 11, further comprising:
   making a measurement of a property of the earth formation;
   estimating an elapsed time between a time of drilling the borehole through the earth formation and a time of the measurement;
   estimating the temperature of the earth formation based on the elapsed time, a temperature of drilling fluid over the elapsed time, a virgin formation temperature, a thermal conductivity of the earth formation and a heat capacity of the earth formation; and
   verifying the accuracy of the estimated temperature by comparing the estimated temperature to the temperature calculated from the NQR signal.

19. The method of claim 11, further comprising:
   making a measurement of a property of the earth formation;
   estimating an elapsed time between a time of detecting the NQR signal and a time of the measurement; and
   estimating the temperature of the earth formation at the time of measurement based on the elapsed time, a temperature of drilling fluid over the elapsed time, the temperature calculated from the NQR resonance signal, a thermal conductivity of the earth formation and a heat capacity of the earth formation.

20. The method of claim 11, wherein the method is performed during an operation selected from a drilling operation and a logging operation.

21. The system of claim 1, wherein the downhole tool is configured to be movable within the borehole.

* * * * *